US008172752B2

(12) United States Patent
Russ (10) Patent No.: US 8,172,752 B2
(45) Date of Patent: May 8, 2012

(54) AUTOMATIC WIRELESS PAN/LAN SWITCHING

(75) Inventor: Tomas Russ, Carlisle, MA (US)

(73) Assignee: Draeger Medical Systems, Inc., Andover, MA (US)

( * ) Notice: Subject to any disclaimer, the term of this patent is extended or adjusted under 35 U.S.C. 154(b) by 0 days.

(21) Appl. No.: 12/824,915

(22) Filed: Jun. 28, 2010

(65) Prior Publication Data

US 2010/0280339 A1 Nov. 4, 2010

Related U.S. Application Data

(63) Continuation of application No. 11/259,737, filed on Oct. 26, 2005, now abandoned.

(60) Provisional application No. 60/623,706, filed on Oct. 29, 2004.

(51) Int. Cl.
*A61B 5/00* (2006.01)
*H04M 1/66* (2006.01)

(52) U.S. Cl. ............... 600/300; 600/301; 340/10.52; 455/410; 455/411

(58) Field of Classification Search .............. None
See application file for complete search history.

(56) References Cited

U.S. PATENT DOCUMENTS

| | | | |
|---|---|---|---|
| 6,213,942 B1 | 4/2001 | Flach et al. | |
| 6,221,012 B1 | 4/2001 | Maschke et al. | |
| 6,497,656 B1 | 12/2002 | Evans et al. | |
| 6,525,854 B1 | 2/2003 | Takahashi et al. | 359/143 |
| 6,544,174 B2 | 4/2003 | West et al. | |
| 6,589,170 B1 | 7/2003 | Flach et al. | |
| 6,616,606 B1 | 9/2003 | Petersen et al. | |
| 6,654,631 B1 * | 11/2003 | Sahai | 600/509 |
| 6,749,566 B2 | 6/2004 | Russ | |
| 6,819,013 B2 * | 11/2004 | Kelly et al. | 307/104 |
| 6,870,475 B2 * | 3/2005 | Fitch et al. | 340/539.12 |
| 7,061,924 B1 * | 6/2006 | Durrant et al. | 370/401 |
| 7,316,648 B2 * | 1/2008 | Kelly et al. | 600/300 |
| 2001/0034475 A1 | 10/2001 | Flach et al. | |
| 2002/0013518 A1 * | 1/2002 | West et al. | 600/300 |
| 2002/0084698 A1 * | 7/2002 | Kelly et al. | 307/104 |
| 2002/0115914 A1 * | 8/2002 | Russ | 600/300 |
| 2003/0206116 A1 | 11/2003 | Weiner et al. | |
| 2003/0220673 A1 | 11/2003 | Snell | |
| 2004/0004460 A1 | 1/2004 | Fitch et al. | 320/108 |
| 2004/0147818 A1 | 7/2004 | Levy et al. | 600/300 |
| 2005/0138428 A1 | 6/2005 | McAllen | |

FOREIGN PATENT DOCUMENTS

EP 0 796 590 A1 9/1997

* cited by examiner

*Primary Examiner* — Sam Yao
*Assistant Examiner* — Shirley Jian
(74) *Attorney, Agent, or Firm* — Mintz, Levin, Cohn, Ferris, Glovsky and Popeo P.C.

(57) ABSTRACT

A communication system is used by a portable patient monitoring device for connecting to other devices, including a docking station, via one or more networks. The communications system includes an adaptive communication interface which, when the patient monitoring device is docked, establishes communication with a first network, and receives from a first docking station a first unique identifier that identifies the first docking station, allowing the patient monitoring device to communicate patient parameters to the first destination. While the portable patient monitoring device is undocked, the adaptive communication interface is inhibited from establishing communication with a network providing an identifier to the portable patient monitor that does not match the first unique identifier. Upon docking to a second docking station, the patient monitoring device establishes communication with a second network using a new unique identifier received from the second docking station via a second exclusive communication link.

13 Claims, 3 Drawing Sheets

AUTOMATIC WIRELESS PAN/LAN SWITCHING

CROSS-REFERENCED TO RELATED APPLICATION

This application is a continuation of the U.S. patent application Ser. No. 11/259,737, filed Oct. 26, 2005, now abandoned which claims the benefit of U.S. Provisional Application Ser. No. 60/623,706, filed Oct. 29, 2004, the contents of which are incorporated herein by reference in their entirety.

FIELD OF THE INVENTION

The present invention relates to the field of patient monitoring and/or treatment devices which may be connected to hospital local area networks (LANs), and more specifically, to patient monitoring and/or treatment devices which may be coupled to hospital LANs via more than one communications channel.

BACKGROUND OF THE INVENTION

In hospital environments, patients often require continual monitoring with relatively short repetition intervals, even when the patient is being transported from one location in the hospital to another. Portable patient monitors have been developed which are battery operated and are able to travel with the patient to provide uninterrupted patient monitoring. Portable patient monitors may include electrodes attached to a patient to receive electrical signals representing physiological parameters of the patient. These parameters may be displayed on the portable patient device, but may also be supplied to a central location in the hospital where they may be displayed on a patient monitoring system, or stored in a patient medical record or a patient data repository.

In such a hospital environment, docking stations for portable devices are provided at fixed locations throughout the hospital, such as patient rooms, therapy rooms, operating rooms, and so forth. Such docking stations permit the batteries in the portable patient monitor to be recharged and also permit the portable patient monitor to be connected to the central location through a wired link from the docking station to the central location. It is also possible for the portable patient monitor to remain in communication with the docking station when undocked in proximity of the docking station. For example, the portable patient monitor may be undocked within a therapy room to allow the patient to exercise without the restraint of being attached to the docking station. When the patient is being moved from one location to another, the portable patient monitor may remain in communication with the central location wirelessly. To do this, wireless access points with associated antennae are located throughout the hospital, e.g. in hallways, elevators, etc.; wherever a patient may be transported from one room to another.

Thus, a portable patient monitor may include multiple channels for maintaining communication with the central location of the hospital. It is desirable that transitions between communications channels be handled properly so that continual monitoring may be maintained.

BRIEF SUMMARY OF THE INVENTION

In accordance with principles of the present invention, a communication system is used by a portable patient monitoring device in connecting to a plurality of other devices, including a docking station suitable for attaching to the portable patient monitoring device. The portable patient monitoring device processes signal parameters acquired from a patient. The communications system includes an adaptive communication interface for automatically operating in a first mode of operation when the portable patient monitoring device is attached to the docking station. In the first mode of operation the portable patient monitor receives an identifier identifying a particular docking station via a first wireless communication link exclusively between the docking station and the portable patient monitoring device, in response to detecting the portable patient monitoring device is attached to the docking station. Patient parameters acquired via the first wireless communication link are communicated to a destination associated with the particular docking station identified by the received identifier. In a second mode of operation when the portable patient monitoring device is unattached to the docking station, the portable patient monitor establishes a second wireless communication link between the portable processing device and a network, in response to detecting the first communication link is non-operational. Patient parameters acquired via the second wireless communication link are communicated to a destination.

DETAILED DESCRIPTION OF THE INVENTION

A processor, as used herein, operates under the control of an executable application to (a) receive information from an input information device, (b) process the information by manipulating, analyzing, modifying, converting and/or transmitting the information, and/or (c) route the information to an output information device. A processor may use, or comprise the capabilities of, a controller or microprocessor, for example. The processor may operate with a display processor or generator. A display processor or generator is a known element for generating signals representing display images or portions thereof. A processor and a display processor comprises any combination of, hardware, firmware, and/or software.

An executable application, as used herein, comprises code or machine readable instructions for conditioning the processor to implement predetermined functions, such as those of an operating system, remote patient monitoring system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters.

Figure 1:
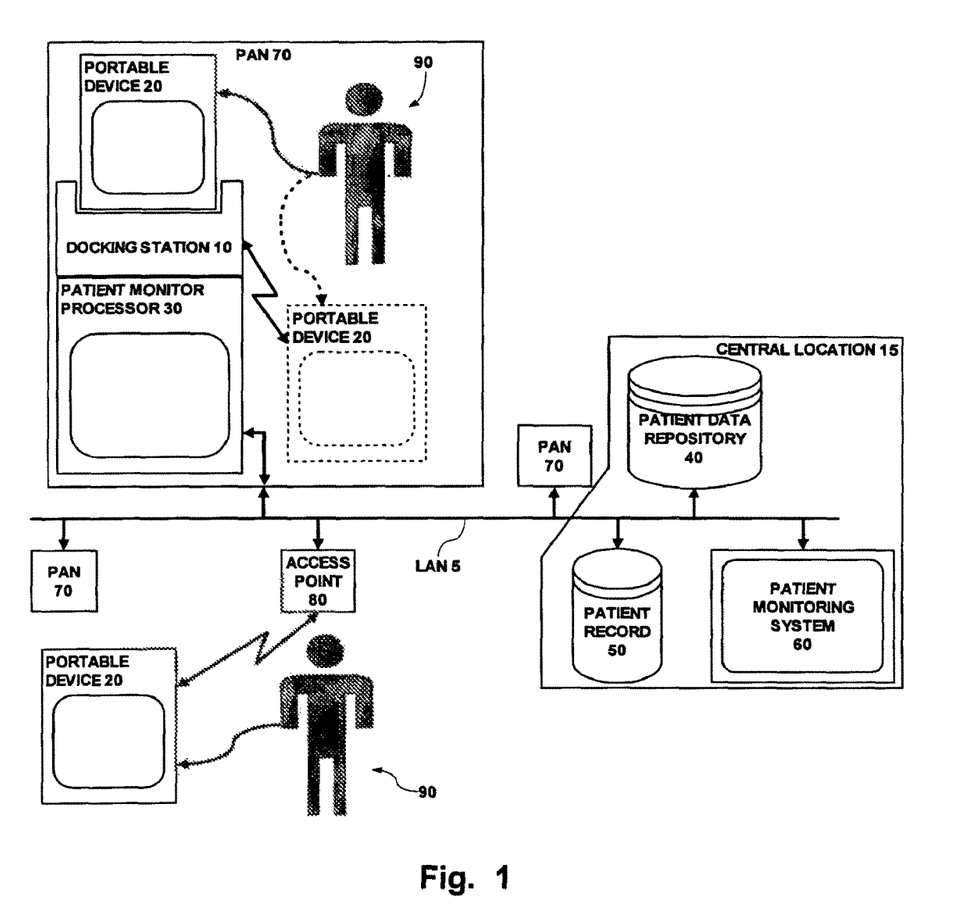
FIG. 1 is a block diagram of respective communications channels between a portable patient monitor and a hospital central location.

FIG. 1 is a block diagram of respective communications channels between a portable patient monitor 20 and a hospital central location 15. In FIG. 1, a hospital central location 15 includes a patient data repository 40, a patient medical record 50 and a patient monitoring system 60 coupled together via a local area network (LAN) 5. The LAN 5 is also coupled to a plurality of patient area networks (PAN) 70, which are described in more detail below. The LAN 5 is also coupled to an access point 80.

A patient area network (PAN) 70 may include a plurality of patient monitoring and/or treatment devices which are coupled together via a network. Typically, PANs 70 are located in fixed locations in the hospital where diagnosis, monitoring and treatment of a patient may be performed, such as in a patient room a therapy room, an operating room, a diagnostic test room (e.g. X-ray, CAT scan, etc.), and so forth. The respective PANs 70 are assigned a unique identifier which is used to identify messages to and from the PAN 70. The unique identifier may also be used to determine a geographical location of the PAN 70.

At the top left of FIG. 1, a particular PAN 70 is illustrated in more detail. In this PAN 70, a patient 90 has sensors (not shown) attached to him to generate various signals which may be processed to derive physiological parameters of that patient, such as (a) electrocardiograph (ECG) data, (b) blood parameter data, (c) ventilation parameter data, (d) infusion pump related data, (e) blood pressure data, (f) pulse rate data, and (g) temperature data. These signals are coupled to a portable patient monitor device 20. The portable patient monitor device 20 includes circuitry for processing these signals to generate patient physiological parameters, and a display screen for displaying the physiological parameters for a clinician. The portable patient monitor device 20 may be physically and electrically coupled to a docking station 10. The docking station 10 is coupled to a patient monitor processor 30. The patient monitor 30 may provide processing capabilities beyond what the portable patient monitor device 20 alone has, and also includes a link, termed a bridge, between the PAN 70 and the LAN 5. This permits the patient monitor processor 30 to access data at the central location 15 and to display this data on the patient monitor 30.

In operation, the destination of the patient physiological parameter data from the portable patient monitor device 20 is the central location 15. Also, because the unique identifier identifying the network node sending the patient physiological parameter data to the central location 15 is associated with a docking station 10, and because the geographical location of the docking station 10 is known, the unique identifier enables determination of the geographical location of the docking station 10. A map may be maintained in the central location 15 associating the identifier with a geographical location. The central location 15 may display the patient physiological parameter data on the patient monitoring system 60. This permits the medical status of one or more patients to be monitored at a single location. The patient physiological parameter data may also be stored in a patient medical record 50. This data may be reviewed by a physician or other clinician as part of a diagnosis or treatment process. The patient physiological parameter data may also be stored in a patient data repository 40, providing for longer term storage and retrieval of patient data.

When the docking station 10 detects that the portable patient monitor device 20 has been docked, it initiates a first mode of operation. In this mode of operation, the portable patient monitor device 20 is configured to connect to the LAN 5 via the docking station 10 and the patient monitor processor 30, in a manner described in more detail below. This mode of operation may continue even if the portable patient monitor device 20 is undocked from the docking station 10. This is illustrated in phantom in FIG. 1. If the portable patient monitor device 20 remains in relative proximity to the docking station 10, then a wireless link may be maintained between the portable patient monitor device 20 and the docking station 10, allowing the portable patient monitor device 20 to continue to communicate with the central location 15 via the docking station 10 and the patient monitor processor 30.

At the bottom left of FIG. 1, a wireless access point 80 is coupled to the LAN 5. Typically, the wireless access points 80 are located at locations in the hospital where patients may be transported, but which are not in fixed locations where a docking station 10 and patient monitor processor 30 may be placed, such as a hallway, elevator, and so forth. A portable patient monitor device 20 is illustrated as being connected to a patient 90. In this case, the portable patient monitor device 20 is not in close proximity to a docking station 10 or patient monitor processor 30. The portable patient monitor device 20 includes a wireless link which may connect to the LAN 5 via the wireless access point 80. In this situation, the portable patient monitor device 20 is configured to operate in a second mode of operation. In this mode of operation, the portable patient monitor device 20 communicates patient physiological parameter data to the central location 15 via the LAN 5.

Figure 2:
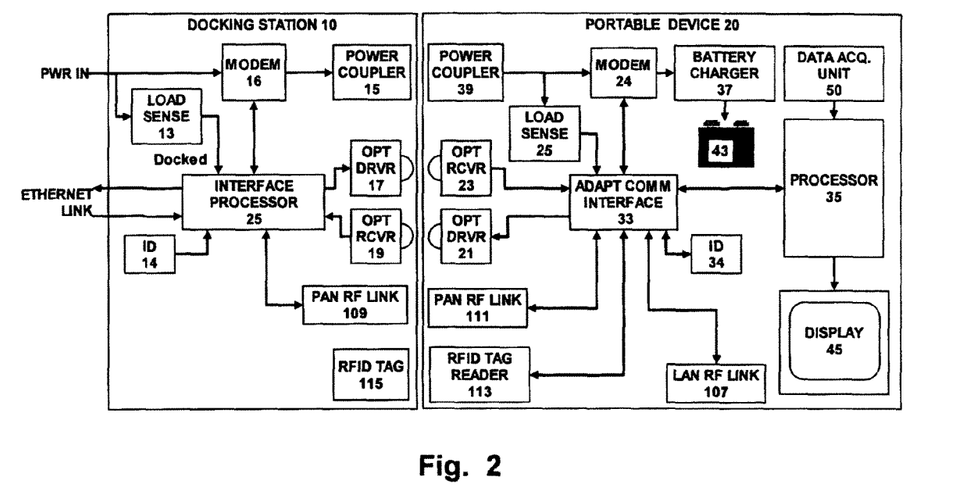
FIG. 2 is a block diagram of a portable patient monitor and a docking station according to principles of the present invention.

FIG. 2 is a block diagram of a portable patient monitor device 20 and a docking station 10 according to principles of the present invention. In FIG. 2, those elements which are the same as those illustrated in FIG. 1 are designated by the same reference number. In FIG. 2, a source of electrical power (not shown) is coupled to a power input terminal (PWR IN) of a docking station 10. The power input terminal is coupled to respective input terminals of a load sense circuit 13 and a modulator/demodulator (modem) 16. An output terminal of the modem 16 is coupled to an input terminal of a power coupler 15. A bidirectional Ethernet link is coupled to a network connection (not shown), such as the LAN 5, or to LAN 5 via a patient monitor processor 30 (also not shown). The Ethernet link is coupled to a first communication terminal of an interface processor 25. A second communication terminal of the interface processor 25 is coupled to an optical link, e.g. optical driver 17 and optical receiver 19. A third communications terminal is coupled to a PAN RF link 109. A fourth communications terminal is coupled to the modem 16. A first control input terminal is coupled to an output terminal of the load sense circuit 13. A second control input terminal is coupled to a source 14 of a unique identifier. A radio frequency identification (RFID) tag 115 is also located on the docking station 10. The RFID tag 115 may be passive, requiring no power, or active, requiring power for operation.

The portable patient monitor device 20 includes a power coupler 39. An output terminal of the power coupler 39 is coupled to respective input terminals of a load sense circuit 25 and a modem 24. An output terminal of the modem 24 is coupled to a battery charger 37. The battery charger is coupled to a battery 43. A data acquisition unit 50 is coupled to a plurality of patient attachable electrodes (not shown) which may be attached to a patient to generate electrical signals representing patient physiological parameter data. An output terminal of the data acquisition unit 50 is coupled to an input terminal of a processor 35. An output terminal of the processor 35 is coupled to an input terminal of a display unit 45. A bidirectional communications terminal of the processor 35 is coupled to a first communications terminal of an adaptive communications interface 33. A second communications terminal of the adaptive communications interface 33 is coupled to a LAN RF link 107. A third communications terminal is coupled to a PAN RF link 111. A fourth communications terminal is coupled to an optical link, e.g. optical driver 21 and optical receiver 23. A fifth communications terminal is coupled to the modem 24. A sixth communications terminal is coupled to an RFID tag reader 113. A control input terminal of the adaptive communications interface 33 is coupled to an output terminal of the load sense circuit 25 and a bidirectional control terminal of the adaptive communications interface 33 is coupled to storage 34 for a unique identifier.

In operation, the portable patient monitor device 20 may be docked in the docking station 10. In this configuration, illustrated in FIG. 2, the power couplers 15 and 39 are physically aligned to pass power from the docking station 10 to the portable patient monitor device 20. For example, the power couplers 15 and 39 may be a split transformer in which the primary winding is in the power coupler 15 and the secondary winding is in the power coupler 39. When docked, the primary winding 15 and secondary winding 39 are magnetically coupled so that power is transferred from the docking station 10 to the portable patient monitor device 20. In the portable patient monitor device 20, the battery charger 37 receives power from the power coupler 39, recharges the battery 43 and maintains it at full charge.

The docking station 10 may detect that the portable patient monitor device 20 is docked by sensing the status of the signal at the power input terminal. For example, when the portable patient monitor device 20 is docked, the current through the power input terminal will be higher than when the portable patient monitor device 20 is undocked. The load sense circuit 13 monitors the signal on the power input terminal and generates a control signal 'Docked' indicating that the portable patient monitor device 20 is docked to the docking station 10. In a similar manner, the load sense circuit 25 in the portable patient monitor device 20 may also detect when it is docked to the docking station 10. Alternatively, the adaptive communications interface 33 in the portable patient monitor device 20 may detect that it is docked to the docking station 10 by detecting that an active communication link is present between the docking station 10 and the portable patient monitor device 20.

When the portable patient monitor device 20 is docked, the optical link in the docking station 10, e.g. optical driver 17 and optical receiver 19, is physically aligned with the optical link in the portable patient monitor device 20, e.g. optical receiver 23 and optical driver 21 respectively. When aligned, it is possible for the interface processor 25 in the docking station 10 to communicate with the adaptive communications interface 33 in the portable patient monitor device 20 via the optical link. Because it is an optical link, this communications link may not receive signals from another location. That is, it is a wireless link which exists exclusively between the docking station 10 and the portable patient monitor device 20.

When the portable patient monitor device 20 is docked to the docking station 10, the modem 16 in the docking station 10 may be configured to receive data from the interface, processor 25 and to modulate the amplitude and/or frequency of the power input signal with that data. The modem 24 in the portable patient monitor device 20 demodulates data received from the interface processor 25 via the modem 16 in the docking station 10, and supplies that data to the adaptive communications interface 33. Correspondingly, the modem 24 in the portable patient monitor device 20 may be configured to receive data from the adaptive communications interface 33 and modulate the amplitude and/or frequency of the power input signal with that data. The modem 16 in the docking station 10 demodulates data received from the adaptive communications interface 33 in the portable patient monitor device 20 via the modem 24, and supplies that data to the interface processor 25. Because this is a magnetically coupled link, this communications link, too, may not receive signals from another location. Thus, it, also, is a wireless link which exists exclusively between the docking station 10 and the portable patient monitor device 20.

The interface processor 25 in the docking station 10 may communicate with the adaptive communications interface 33 in the portable patient monitor device 20 via the PAN wireless link 109, 111. This link may be activated when the portable patient monitor device 20 is docked to the docking station 10 and may remain activated when it is not docked. This link is implemented as an RF link, and thus is subject to receiving signals from other locations. However, the power in the RF link may be constricted so that the range of operation of this link is limited. More specifically, in the illustrated embodiment, the typical range of operation of this link is approximately the size of a room, such as a patient room, operating room, therapy room, etc. However, the power in this link may be controlled so that when the portable patient monitor device 20 is docked, the power is constricted to be low enough that the range of operation is only several inches. In this way, while possible, it is improbable that a signal will be received from another location. Thus, in practical terms, this wireless link exists exclusively between the docking station 10 and the portable patient monitor device 20.

When the portable patient monitor device 20 is attached to the docking station 10, the adaptive communications interface 33 initiates a first mode of operation using a first wireless link. In the first operational mode the portable patient monitor device 20 communicates patient physiological parameter data to a first destination. For example, the portable patient monitor device 20 may send patient physiological parameter data to the patient monitor processor 30 (FIG. 1) via the docking station 10. The patient monitor processor 30 may include a display device larger than the display device on the portable patient monitor device 20 and further processing power. This enables the patient monitor processor 30 to display more sophisticated patient physiological parameter data than possible by the portable patient monitor device 20 alone. Further, the patient monitor processor 30 may communicate with the central location 15, enabling it to retrieve data from the central location 15, such as X-ray images, or laboratory test results and display them for the clinician. Alternatively, the portable patient monitor device 20 may send patient physiological parameter data to the central location 15 via the docking station 10, patient monitor processor 30 and LAN 5. Referring again to FIG. 1, as described above, at the central location, the patient physiological parameter data may be sent to (a) an electronic patient record 50, (b) a patient monitoring system 60, and/or (c) a patient data repository 40.

In order to send and receive messages over the LAN 5 via the Ethernet link from the docking station 10, the portable patient monitor device 20 uses a unique identifier associated with the docking station 10. This identifier may be: (a) an Ethernet compatible MAC address, (b) an IP address, (c) a port identifier, (d) an Internet compatible address and/or (e) a LAN address. Messages sent from the portable patient monitor device 20 include this unique identifier to identify the network node which sent the message. The unique identifier associated with the portable patient monitor device 20 is derived from the docking station 10 to which it is docked.

In order to ensure that the unique identifier assigned to the portable patient monitor device 20 comes from the docking station 10 to which it is docked, the communications channel used to transmit this data is exclusive between the docking station 10 and the portable patient monitor device 20. The unique identifier may be communicated from the docking station 10 to the portable patient monitor device 20 using one of the three wireless links discussed above: (a) the optical link 17, 19, 21, 23; (b) the magnetic link 15, 16, 24, 39; or (c) the PAN RF link 109, 111, with constricted power. More specifically, in the illustrated embodiment, the interface processor 25 in the docking station 10 retrieves the unique identifier from the identifier source 14. The interface processor 25 then establishes one of the communication links described above, and sends the identifier representative data to the adaptive communications interface 33 in the portable patient monitor device 20. The adaptive communications interface 33 receives the identifier representative data and stores it in the identifier store 34.

Alternatively, the RFID tag 115 in the docking station 10 may be encoded to return data representing the unique identifier associated with the docking station 10 when queried. The adaptive communications interface 33 may activate the RFID tag reader 113 to query the RFID tag 115 in the docking station 10 to retrieve the unique identifier. When queried, the RFID tag 115 in the docking station 10 returns a signal carrying the unique identifier representative data to the RFID tag reader 113. The adaptive communications interface 33 receives this signal from the RFID tag reader 113 and stores data representing the unique identifier in the identifier store 34.

One skilled in the art understands that other information may also be stored in the identifier store 34. For example: (a) an identifier associated with a previous docking station 10 to which the portable patient monitor device 20 was docked prior to the current docking station 10, (b) information representing the time a portable patient monitor device 20 is docked in a docking station 10 and undocked from that docking station 10 (e.g. time stamps), and/or (c) other information derived using the identifier associated with said previous docking station may also be stored in the identifier store 34.

In subsequent communications with the patient monitor processor 30 (FIG. 1) or the central location 15 via the Ethernet link, the adaptive communications interface 33 uses the unique identifier. More specifically, in the illustrated embodiment, after the unique identifier has been received by the portable patient monitor device 20, the portable patient monitor device 20 communicates acquired patient parameters from the data acquisition unit 50 via the first wireless communication link to the first destination e.g. patient monitor processor 30 and/or the central location 15 associated with the particular docking station identified by the unique identifier. More specifically, in the illustrated embodiment, the adaptive communication interface 33 supports communication via the Ethernet link in the docking station 10 using wireless technologies including at least one of, (a) WLAN 802.11b standard compatible communication, (b) 802.11a standard compatible communication, (c) 802.11g standard compatible communication, (d) Bluetooth 802.15 standard compatible communication, (e) GSM/GPRS standard compatible communication, (f) UWB standard compatible communication 802.15.3, and (g) RFID sensing. (The 802.11 standard compatible communications links are sometimes termed WiFi communications links.) Referring again to the bottom left-hand portion of FIG. 1, a patient 90 may also be monitored by an undocked portable patient monitor device 20 outside of a PAN 70. When the portable patient monitor device 20 is not attached to, or in communication with, a docking station 10, the portable patient monitor device 20 operates in a second mode of operation. In this mode of operation, the portable patient monitor device 20 establishes a second wireless link to the network LAN 5. This mode of operation may be established when it is detected that the first more of operation, described above, becomes non-operational. In this mode of operation, the portable patient monitor device 20 communicates patient physiological parameter data to a second destination via the second wireless link. More specifically, in the illustrated embodiment, the second destination may be the central location 15, where the data may be supplied to the patient record 50, the patient monitoring system 60 and/or the patient data repository 40. This second destination may be the same as the first destination, or may be different.

Referring again to FIG. 2, the adaptive communications interface 33 includes circuitry which may monitor the status of established communications links. Specifically, the adaptive communications interface 33 may detect when a communications link becomes non-operational. For example, a status signal from a link, e.g. optical link 21, 23, PAN RF link 111 or the modem 24, may indicate that the link has become non-operational. When it is detected that the first communications link is non-operational, the adaptive communications interface 33 conditions the LAN RF link 107 to attempt to connect to the LAN 5 via an access point 80. In this manner, patient physiological parameter data may be continually supplied from the portable patient monitor device 20 to the central location 15 even if the portable patient monitor device 20 is undocked from the docking station 10 and removed from the vicinity of the PAN 70. One skilled in the art understands that the LAN RF link 107 has a relatively longer range than the PAN RF LINK 111.

It is also possible for a portable patient monitor device 20 to be returned to a PAN 70 from which it was removed, as when a patient returns from a diagnostic testing room to the patient room. The portable patient monitor device 20 may then be redocked in the docking station 10. In this case, communications may be reestablished using the wireless links described above. The manner of transitioning among (a) a communications link used when a portable patient monitor device 20 is docked in a docking station 10, (b) a communications link used when the portable patient monitor device 20 is undocked but is within range of a PAN 70, and (c) a communications link used when a portable patient monitor device 20 is undocked, is not within range of a PAN 70 but is within range of the LAN 5, is described in more detail below.

Figure 3:
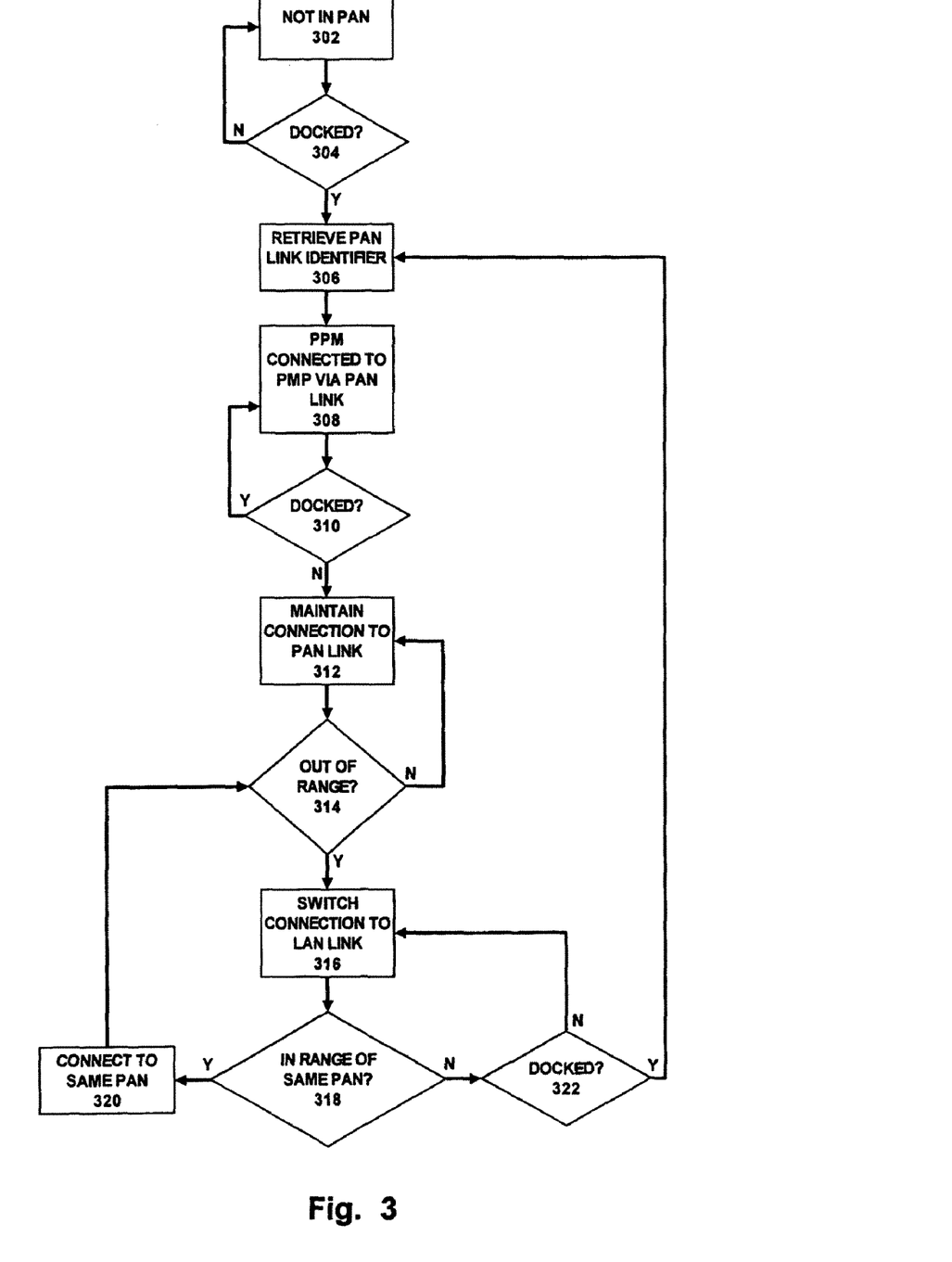
FIG. 3 is a flowchart useful in understanding the operation of the portable patient monitor and docking station illustrated in FIG. 2 according to principles of the present invention.

FIG. 3 is a flowchart useful in understanding the operation of the portable patient monitor 20 and docking station 10 illustrated in FIG. 2 according to principles of the present invention, during the transitions. In the following description, reference will be made to both FIG. 2 and FIG. 3. FIG. 3 begins in step 302 when the portable patient monitor device 20 is not operating within range of a PAN 70. This may, for example, occur when a portable patient monitor device 20 is initially powered on and attached to a patient, or when it is operating within range of the LAN 5 but not within range of a PAN 70. In step 304, the portable patient monitor device 20 determines if it has been docked in a docking station 10. This may be determined via the load sense circuit 25 as described above. In step 306, the unique identifier for the PAN 70 is retrieved from the docking station 10 using a first communications link (e.g. optical link, magnetic link, PAN RF link or RFID link), as described above. In step 308, the portable patient monitor device 20 establishes Ethernet communications with the patient monitor processor 30 via the docking station 10. Patient physiological parameter data from the data acquisition unit 50 are supplied to the first destination (patient monitor processor 30 and/or central location 15) via the first communications link (e.g. optical link, magnetic link, or PAN RF link).

In step 310, the portable patient monitor device 20 monitors whether it is still docked. This may be done by the load sense circuit 25. If the portable patient monitor device 20 remains docked, it maintains the first communications link established in step 308. If the portable patient monitor device 20 becomes undocked, then communications with the PAN 70 is maintained, possibly using a different communications link. This may occur if the portable patient monitor device 20 is undocked from the docking station 10, but remains within the patient room. In this case, in step 312, the adaptive communications interface 33 activates the PAN RF link 109, 111 if it is not already active. The transmission power of the PAN RF link 109, 111 in this mode of operation is substantially higher than the constricted power used by the PAN RF link 109, 111 when the portable patient monitor device 20 is docked in the docking station 10. This enables a transmission range sufficient to cover the patient room. Patient physiological parameter data from the data acquisition unit 50 is communicated over the PAN RF link 109, 111, with substantially higher power, to the patient monitor processor 30 and/or the central location 15 via the docking station 10.

In general, a portable patient monitor device 20 will attempt to remain in communication with the PAN 70 containing the docking station 10 from which it received the unique identifier as long as it remains within range. In step 314 the adaptive communications interface 33 in the portable patient monitor device 20 monitors communication with the docking station 10. So long as the portable patient monitor device 20 remains within range of the docking station 10, the portable patient monitor device 20 communicates with the docking station 10 using the PAN RF communication link 109, 111 in step 312.

If, however, the PAN RF link 109, 111 becomes inoperative, e.g. because the portable patient monitor device 20 goes out of range, then in step 316 the adaptive communications interface 33 activates the LAN RF link 107, establishing a second communications link between the portable patient monitor device 20 and the LAN 5. The patient physiological parameter data from the data acquisition unit 50 is supplied to the central location 15 via the LAN 5 in this mode of operation. As described above, this may occur when a patient is removed from the patient room and taken to e.g. an operating room, diagnostic testing room, therapy room, etc., though the hospital.

The LAN RF link 107 is maintained so long as the portable patient monitor device 20 remains within range of the LAN 5 and out of range of a PAN 70. Because of the varying ranges of PAN RF communication links in the respective PANs 70, the portable patient monitor device 20 may come within range of a PAN RF link during transportation of the patient in the hospital, and/or when the patient arrives at the final destination, if that destination contains a PAN 70. In step 318 the adaptive communications interface 33 determines (a) that the portable patient monitor device 20 is within range of a PAN, and (b) whether the identifier stored in the identifier store 34 matches the identifier of the PAN RF link currently within range, i.e. is the same PAN from which the portable patient monitor device 20 was undocked.

The adaptive communications interface 33 is inhibited from establishing communication with a PAN 70 which fails to provide the previously received unique identifier unless the portable patient monitor device 20 is docked. If a different PAN 70 is detected, then in step 322 the adaptive communications interface 33 in the portable patient monitor device 20 monitors whether the portable patient monitor device 20 is docked. If the portable patient monitor device 20 is docked in the newly entered PAN 70, communication is established between the portable patient monitor device 20 and the new PAN 70 e.g. using the optical link, magnetic link, PAN RF link at constricted power, or RFID link. In step 306 the unique identifier associated with the docking station 10 in the new PAN 70 is retrieved, and in step 308 communications between the portable patient monitor device 20 and the docking station 10 established. Patient physiological parameter data from the data acquisition unit 50 is sent to the patient monitor processor 30 or central location 15 via the docking station 10 in the new PAN 70.

If in step 318 the same PAN is detected, as may happen if the patient is returned to the patient room from which he was originally taken, then in step 320 the adaptive communications interface 33 in the portable patient monitor device 20 activates the PAN RF link 109, 111, with substantially higher power. This reestablishes the first communications link with the docking station 10. In this case, patient physiological parameter data from the data acquisition unit 50 is sent to the patient monitor processor 30 or central location 15 through the docking station 10 via the PAN RF link 109,111. In step 314, the adaptive communications interface 33 in the portable patient monitor device 20 monitors the PAN RF link 109, 111 to detect if the portable patient monitor device 20 goes out of range.

The embodiment above is described as having multiple communications links available, e.g. five links: (1) optical link 17, 19, 21, 23; (2) magnetic link 15, 16, 24, 39; (3) PAN RF link 109, 111; (4) LAN RF link 107; and (5) RFID link 113, 115. One skilled in the art, however, understands that different combinations of communication links may be available in the portable patient monitor device 20 and docking station 10.

For example, in another configuration, the portable patient monitor device 20 may have three links: (1) a short-range wireless PAN link e.g. the optical link 17, 19, 21, 23, used by the docking station 10 to communicate the unique identifier to the portable patient monitor device 20 and by the portable patient monitor device 20 to communicate patient physiological parameter data to the patient monitor processor 30 and/or central location 15 via the docking station 10 when it's docked; (2) a short-range wireless RF PAN link 109, 111 used by the portable patient monitor device 20 to communicate patient physiological parameter data to the patient monitor processor 30 and/or central location 15 via the docking station 10 when it's undocked but within the PAN 70; and (3) a longer-range wireless link used by the portable patient monitor device 20 to communicate patient physiological parameter data to the central location 15 via the LAN 5 when it's undocked and not within the PAN 70.

Another exemplary configuration includes two links: (1) a short-range wireless RF PAN link 109, 111 used by the docking station 10 to communicate the unique identifier to the portable patient monitor device 20 in a constricted power mode, and by the portable patient monitor device 20 to communicate patient physiological parameter data to the patient monitor processor 30 and/or central location 15 when it's within range of the docking station 10; and (2) a longer-range wireless link used by the portable patient monitor device 20 to communicate patient physiological parameter data to the central location 15 via the docking station 10 when it's undocked and not within the PAN 70.

Another exemplary configuration includes a single link: a wireless link for communicating between the portable patient monitor device 20 and the docking station 10. That is, the first and second wireless communication links are the same link used in different first and second communication modes. In this case, the single link may operate in two different operational modes. For example, a Bluetooth RF link may operate in a very low power mode when the portable patient monitor device 20 is communicating with the docking station 10 within a PAN 70, and in a high power mode when communicating directly with the LAN 5. Alternatively, the single link may be a WiFi (802.11 standard) communications link which operates in the "ad-hoc" mode when communicating with the docking station 10 within a PAN and in "station" mode when communicating directly to the LAN 5.

In this manner, the adaptive communications interface 33 in the portable patient monitor device 20 automatically, and without user intervention, remains in continual communication with either the patient monitor processor 30 in the PAN 70 and/or with the central location 15 via the LAN 5. Once associated with a particular PAN 70 by receiving and using the unique identifier associated with that PAN 70, it communicates through that PAN 70 as long as it remains within range. Otherwise it communicates with the LAN 5.

What is claimed is:

1. A communication system configured to connect a portable patient monitoring device to a plurality of networks via separate communication links, comprising:
   a first patient area network including a first docking station and a first destination;
   a second patient area network, different from the first patient area network, including a second docking station and a second destination; and
   a portable patient monitoring device including an adaptive communication interface configured to:
      establish communication with the first patient area network when the portable patient monitoring device is docked to the first docking station, receive a first unique identifier from the first docking station via a first exclusive communication link between the first docking station and the portable patient monitoring device, and transmit patient parameters to the first destination via the first exclusive communication link, and
      maintain communication with the first patient area network when the portable patient monitoring device is undocked from the first docking station and the first exclusive communication link is inoperative, by establishing a first wireless communication link between the portable patient monitoring device and the first patient area network and obtaining the first unique identifier from the first patient area network via the first wireless link, and transmit patient parameters via the first wireless communication link to the first destination,
      when the portable patient monitoring device is undocked and is in an area where the first and second patient area networks overlap and are within range of the patient monitoring device, the adaptive communication interface is configured to maintain connection with the first patient area network, and is actively inhibited from establishing communication with the second network when the second network provides an identifier that does not match the first unique identifier, and
      when the portable patient monitoring device is docked to the second docking station, the adaptive communication interface is configured to establish a second exclusive communication with the second patient area network, receive a second unique identifier from the second docking station via the second exclusive communication link between the second docking station and the portable patient monitoring device, and transmit patient parameters to the second destination.

2. The communication system of claim 1, wherein the first destination is different from the second destination.

3. The communication system of claim 1, wherein the first destination is identical to the second destination.

4. The communication system of claim 1, wherein each of the first and second unique identifiers identifies messages to and from at least one of the first and second network.

5. The communication system of claim 1, wherein each of the first and second unique identifier identifies a geographic location of at least one of the first and second docking station.

6. The communication system of claim 1, wherein each of the first and second unique identifiers is part of a message sent from the portable patient monitoring device and identifies the first or second network which sent the message.

7. A method for connecting a portable patient monitoring device to a plurality of networks via separate communication links, comprising:
   when the portable patient monitoring device is docked to a first docking station associated with a first network defining a first destination,
      establishing communication with the first network,
      receiving from the first docking station via a first exclusive communication link between the first docking station and the portable patient monitoring device a first unique identifier that identifies the first docking station, and
      transmitting patient parameters to the first destination,
   when the portable patient monitoring device is undocked from the first docking station and the first exclusive communication link is inoperative,
      establishing a first wireless communication link between the portable patient monitoring device and the first network,
      obtaining the first unique identifier from the first network via the first wireless link,
      maintaining communication with the first network, and transmitting patient parameters via the first wireless communication link to the first destination,
   when the portable patient monitoring device is docked to a second docking station associated with a second network different from the first network and defining a second destination,
      establishing a second exclusive communication with a second network,
      receiving from the second docking station via the second exclusive communication link between the second docking station and the portable patient monitoring device a second unique identifier that identifies the second docking station, and
      transmitting patient parameters to the second destination, and
   when the portable patient monitoring device is undocked and is in an area where the first and second patient area networks overlap and are within range of the patient monitoring device,
      maintaining connection with the first network, and actively inhibiting communication with the second network when the second network provides an identifier to the portable patient monitoring device that does not match the first unique identifier.

8. The method of claim 7, wherein the first destination is different from the second destination.

9. The method of claim 7, wherein the first destination is identical to the second destination.

10. The method of claim 7, wherein each of the first and second unique identifiers identifies messages to and from at least one of the first and second network.

11. The method of claim 7, wherein each of the first and second unique identifiers identifies a geographic location of at least one of the first and second docking station.

12. The method of claim 7, wherein the unique identifier is part of a message sent from the portable patient monitoring device and identifies the first or second network which sent the message.

13. A communication system configured to connect a portable patient monitoring device to a plurality of networks via separate communication links, comprising:
 a first patient area network including a first docking station and a first destination;
 a second patient area network, different from the first patient area network, including a second docking station and a second destination; and
 a portable patient monitoring device including an adaptive communication interface configured to:
  establish communication with the first patient area network when the portable patient monitoring device is docked to the first docking station, receive a first unique identifier from the first docking station via a first exclusive communication link between the first docking station and the portable patient monitoring device, and transmit patient parameters to the first destination via the first exclusive communication link, and
  maintain communication with the first patient area network when the portable patient monitoring device is undocked from the first docking station and the first exclusive communication link is inoperative, by establishing a first wireless communication link between the portable patient monitoring device and the first patient area network and obtaining the first unique identifier from the first patient area network via the first wireless link, and transmit patient parameters via the first wireless communication link to the first destination,
 when the portable patient monitoring device is undocked and is in an area where the first patient area network is not within range and the second network is within range, the adaptive communication interface is configured to establish connection with a third network different from the first and second networks when the third network provides an identifier that matches the first unique identifier, and is actively inhibited from establishing communication with the second network when the second network provides an identifier that does not match the first unique identifier, and
 when the portable patient monitoring device is docked to the second docking station, the adaptive communication interface is configured to establish communication with the second patient area network, receive a second unique identifier from the second docking station via a second exclusive communication link between the second docking station and the portable patient monitoring device, and transmit patient parameters to the second destination.

* * * * *